(12) United States Patent
Simpson et al.

(10) Patent No.: US 9,546,357 B2
(45) Date of Patent: Jan. 17, 2017

(54) UGT8 MINI-PROMOTERS

(71) Applicant: The University of British Columbia, Vancouver (CA)

(72) Inventors: Elizabeth M. Simpson, Vancouver (CA); Cletus D'Souza, Vancouver (CA); Charles de Leeuw, Seattle, WA (US); Daniel Goldowitz, Port Moody (CA); Robert A. Holt, North Vancouver (CA); Elodie Portales-Casamar, Vancouver (CA); Vikramjit Chopra, Vancouver (CA); Wyeth W. Wasserman, Vancouver (CA); Steven J. Jones, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 14/644,640

(22) Filed: Mar. 11, 2015

(65) Prior Publication Data

US 2015/0259691 A1    Sep. 17, 2015

Related U.S. Application Data

(60) Provisional application No. 61/951,378, filed on Mar. 11, 2014.

(51) Int. Cl.
*C12N 15/113* (2010.01)
*C12N 9/10* (2006.01)
*C12N 15/85* (2006.01)

(52) U.S. Cl.
CPC ............. *C12N 9/1051* (2013.01); *C12N 15/85* (2013.01)

(58) Field of Classification Search
None
See application file for complete search history.

*Primary Examiner* — Antonio Galisteo Gonzalez
(74) *Attorney, Agent, or Firm* — Pamela J. Sherwood; Bozicevic, Field & Francis LLP

(57) ABSTRACT

Isolated polynucleotides comprising a UGT8 mini-promoters are provided. The mini-promoter may be operably linked to an expressible sequence, e.g. reporter genes, genes encoding a polypeptide of interest, regulatory RNA sequences such as miRNA, siRNA, anti-sense RNA, etc., and the like. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, e.g. for identifying or labeling cells, monitoring or tracking the expression of cells, gene therapy, etc.

10 Claims, 3 Drawing Sheets
(3 of 3 Drawing Sheet(s) Filed in Color)

A Ple240-lacZ
(*UGT8* RRs)

B Ple240-lacZ (*UGT8* RRs)

C Ple240-lacZ
(*UGT8* RRs)

US 9,546,357 B2

UGT8 MINI-PROMOTERS

FIELD OF THE INVENTION

The invention relates to gene promoters and regulatory elements. More specifically, the invention relates to novel UGT8 promoter compositions and related methods.

BACKGROUND

The UGT8 gene encodes the UDP glycosyltransferase 8A, catalyzing the transfer of galactose to ceramide, a key enzymatic step in the biosynthesis of galactocerebrosides, which are abundant sphingolipids of the myelin membrane of the CNS and PNS. This biological function implicates UGT8 as an important gene in oligodendrocyte function. The expression pattern on the Allen Brain Atlas data indicates that this gene is expressed along axonal tracks—this in situ hybridization data is consistent with expression in oligodendrocytes. *Schulte and Stoffel* (1993) demonstrated that the expression is restricted to oligodendrocyte-containing layers of the cerebrum and cerebellum, showing the same expression distribution in brain as myelin basic protein.

There is a need for characterized human UGT8 promoters for gene expression, for instance in human gene therapy applications. It is in particular useful to identify small promoter elements that are sufficient to drive expression in certain cell types, for instance retinal cells. Such small promoter elements, or "mini-promoters" are particularly useful in certain applications, for instance they are more amenable to insertion into viral vectors used in gene therapy applications.

SUMMARY OF THE INVENTION

The present invention provides novel nucleic acid sequence compositions and methods relating to minimal human UGT8 promoters. The invention is based in part on the surprising discovery that certain minimal UGT8 promoter elements are capable of expressing in specific cell types, for instance in cells of the brain or eye.

In one embodiment of the invention, there is provided an isolated nucleic acid fragment comprising an UGT8 mini-promoter, wherein the UGT8 mini-promoter comprises one or more UGT8 regulatory elements operably linked in a non-native conformation to a UGT8 basal promoter. The UGT8 mini-promoter may have a nucleic acid sequence which is substantially similar in sequence and function to SEQ ID NO: 1 or 2. The UGT8 basal promoter may have a nucleic acid sequence which is substantially similar in sequence and function to SEQ ID NO: 3 or 4. The UGT8 regulatory element may have a nucleic acid sequence which is substantially similar in sequence and function to one or more of SEQ ID NO: 5-10, e.g. comprising one, two, three, four or five of the regulatory elements set forth in the provided sequences. The UGT8 mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising an UGT8 mini-promoter, wherein the UGT8 mini-promoter comprises one or more UGT8 regulatory elements operably linked in a non-native conformation to an UGT8 basal promoter. The UGT8 mini-promoter may have a nucleic acid sequence which is substantially similar in sequence and function to SEQ ID NO: 1 or 2. The UGT8 basal promoter may have a nucleic acid sequence which is substantially similar in sequence and function to one or more of SEQ ID NO: 3 or 4. The one or more UGT8 regulatory elements may have a nucleic acid sequence which is substantially similar in sequence and function to SEQ ID NO: 5-10. The UGT8 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell an expression vector comprising an UGT8 mini-promoter element, wherein the UGT8 mini-promoter element comprises one or more UGT8 regulatory elements operably linked in a non-native conformation to an UGT8 basal promoter element. Cells of interest include, without limitation, cells of the peripheral or central nervous system and progenitors thereof, e.g. embryonic stem cells, neural stem cells, neurons, glial cells, astrocytes, microgial cells, etc; and/or cells in the eye and progenitors thereof, e.g. retinal cells, Muller glia cells, etc. The UGT8 mini-promoter may have a nucleic acid sequence which is substantially similar in sequence and function to SEQ ID NO: 1 or 2. The UGT8 basal promoter may have a nucleic acid sequence which is substantially similar in sequence and function to SEQ ID NO: 3 or 4. The UGT8 regulatory element may have a nucleic acid sequence which is substantially similar in sequence and function to one or more of SEQ ID NO: 5-10. The UGT8 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising an UGT8 mini-promoter element, wherein the UGT8 mini-promoter element comprises one or more UGT8 regulatory element operably linked in a non-native conformation to a UGT8 basal promoter element, and wherein the expressible sequence comprises a reporter gene. The UGT8 mini-promoter element may have a nucleic acid sequence substantially similar in sequence and function to SEQ ID NO: 1 or 2. The UGT8 basal promoter element may have a nucleic acid sequence substantially similar in sequence and function to SEQ ID NO: 3 or 4. The UGT8 regulatory element may have a nucleic acid sequence substantially similar in sequence and function to one or more of SEQ ID NO: 5-10. In some embodiments, the cell is a peripheral or central nervous system cell or progenitors thereof, including, without limitation, embryonic stem cells, neural stem cells, glial cells, astrocytes, neurons and the like, and/or cells in the eye and progenitors thereof, e.g. retinal cells, retinal Muller glia, etc. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell an expression vector comprising an UGT8 mini-promoter element operably linked to an expressible sequence, wherein the UGT8 mini-promoter element comprises one or more UGT8 regulatory elements operably linked in a non-native conformation to an UGT8 basal promoter element, and wherein the expressible sequence comprises a reporter gene; and 2) detecting the expression of the reporter gene in the cell of in progeny of the cell as a means of determining the lineage, identity or developmental state of the cell or cell progeny. The UGT8 mini-promoter element may have a nucleic acid sequence substantially similar in sequence and function to SEQ ID NO: 1 or 2. The UGT8 basal promoter element may have a nucleic acid sequence substantially similar in sequence and function to SEQ ID NO: 3 or 4. The UGT8 regulatory element may have a nucleic acid sequence substantially similar in sequence and function to one or more of SEQ ID NO: 5-10. In some embodiments, the cell is a peripheral or central nervous system cell or progenitors thereof, including, without limitation, embryonic stem cells, neural stem cells, glial cells, neurons and the like. In some embodiments, the cell is an eye cell or progenitor thereof, including without limitation a retinal cell, a retinal Muller glial cell, and the like.

In certain embodiments of the invention, there is thus provided a method of treatment of a subject having a disease or condition of the eye, the method comprising administering to the subject a therapeutically effective dose of a composition comprising an UGT8 mini-promoter element, wherein the UGT8 mini-promoter element comprises one or more UGT8 regulatory elements operably linked in a non-native conformation to an UGT8 basal promoter element. The UGT8 mini-promoter element may have a nucleic acid sequence substantially similar in sequence and function to SEQ ID NO: 1 or 2. The UGT8 basal promoter element may have a nucleic acid sequence substantially similar in sequence and function to SEQ ID NO: 3 or 4. The UGT8 regulatory element may have a nucleic acid sequence substantially similar in sequence and function to SEQ ID NO: 5-10. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy. The therapeutic or beneficial compound may be a light-sensitive compound, for instance rhodopsin, channel rhodopsin, etc.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
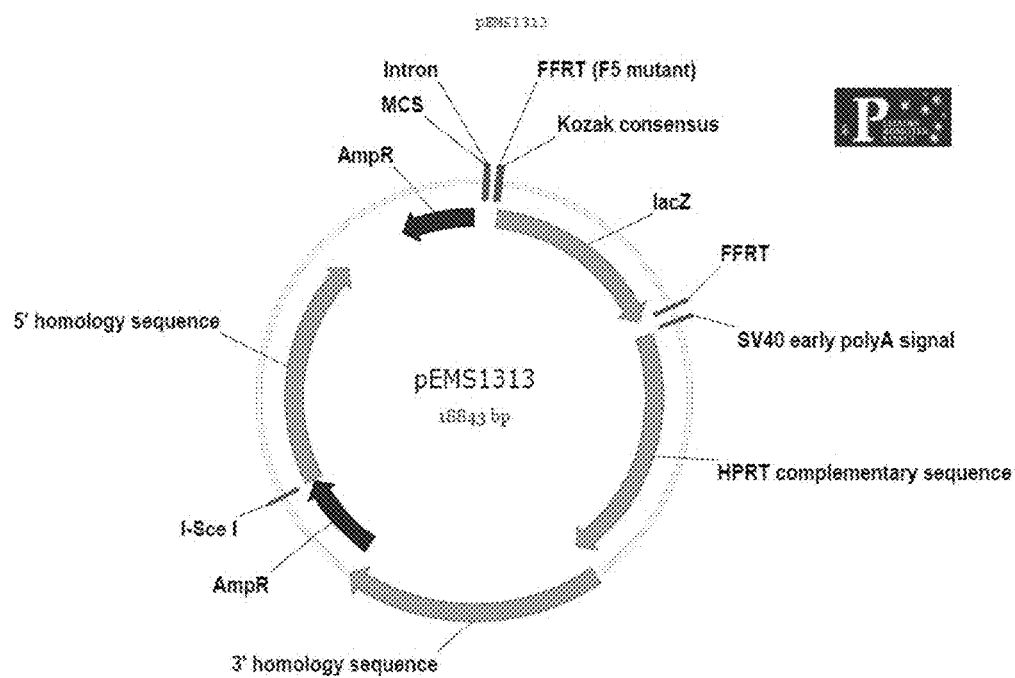
FIG. 1—DNA expression vector (pEMS1313) into which UGT8 promoter elements were inserted for expression studies. The UGT8 promoter with a nucleic acid sequence corresponding to SEQ ID NO: 1 or 2 was inserted into the multiple cloning site (MCS) of the pEMS1313 vector such that it became operably linked to the lac Z reporter gene. The final construct, called Ple240 (containing SEQ ID NO: 1) or Ple267 (containing SEQ ID NO: 2), also contained the HPRT genomic targeting sequence, an ampicillin resistance gene (AmpR) for screening, and a transcriptional termination sequence (SV40 polyA), as well as other elements necessary for vector replication and gene expression.
Figure 2:
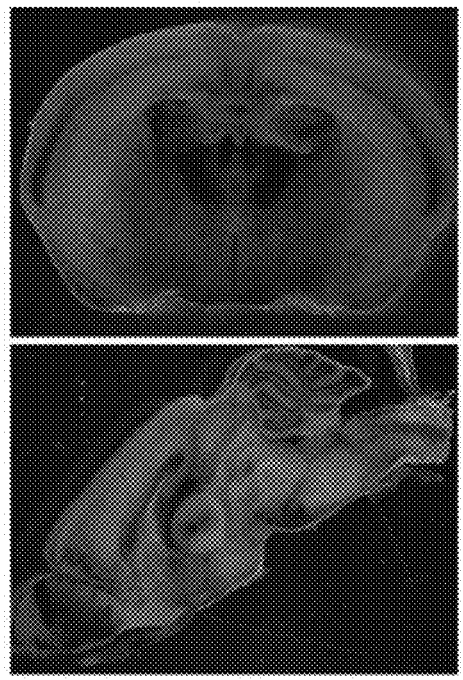
FIG. 2—Ple240 (UGT8 RRs) express in regions containing glia in the mouse brain and eye. The Ple240 promoter driving beta-galactosidase expression was constructed and knocked-in as a single-copy at the mouse Hprt locus for reproducible expression. Adult mice were harvested via perfusion and stained overnight for lacZ activity (blue), indicative of promoter activity. A, a coronal and sagittal slice of mouse brain shows expression in all white matter regions (associated with oligodendroglia), in cortex layer IV (a known region of oligodendrocytes), and in the olfactory globeruli (an area with extensive myelination). B, similarly there is expression along the nerve bundles exiting the spinal cord, which are consistent with Schwann cells (the oligodendroglia outside of the CNS). C, in the mouse eye we see the long processes spanning the entire retina with nuclei in the inner nuclear layer (indicative of Müller glia cells; the supportive glia in the retina).
Figure 2:
Figure 2:
Figure 3:
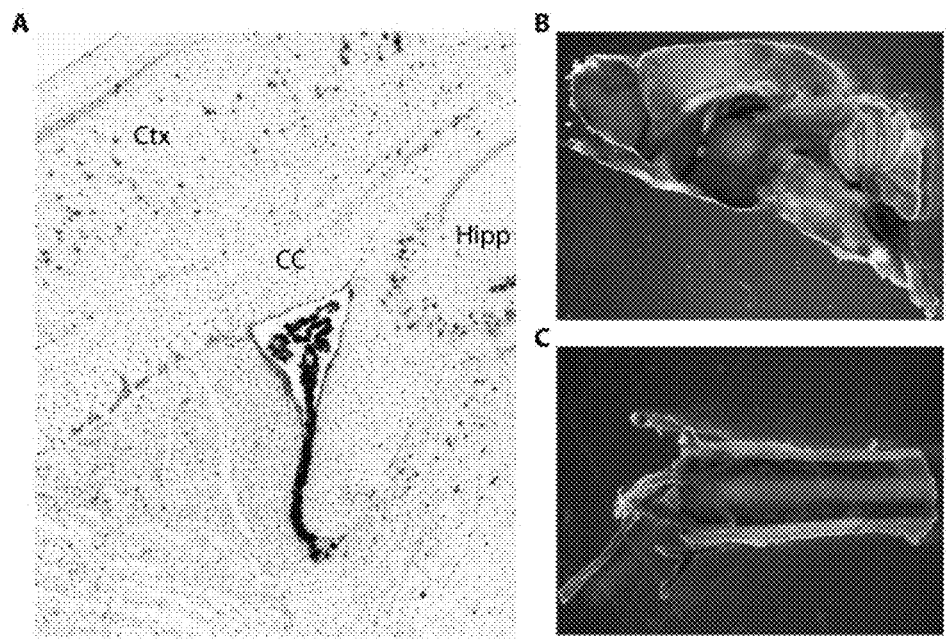
FIG. 3—Ple267 (UGT8 RRs) express in regions containing glia in the mouse brain and spinal cord. The Ple267 promoter driving icre expression was constructed and ssAAV9 virus generated (vEMS40). P0 mice were injected intravenously with virions and mice were harvested at P56 via perfusion and stained overnight for lacZ activity (blue), indicative of promoter activity. A, a sagittal cryosection of mouse brain shows expression in the cortex (Ctx) and corpus callosum (CC), with "puffy" cell bodies indicative of oligodendrocytes and consistent with their known location. B, in a sagittal 1-mm brain section, areas of white matter are often stained positive. C, similarly there is expression along the nerve bundles exiting the spinal cord, which are consistent with Schwann cells (the oligodendroglia outside of the CNS).

The compositions of the present invention include novel polynucleotides comprising UGT8 promoter elements (also referred to herein as UGT8 mini-promoters) as well as novel expression vectors comprising said UGT8 promoter elements (or mini-promoters). The present invention also includes various methods utilizing these novel UGT8 promoter (or mini-promoter) elements or expression vectors.

The term 'UGT8' refers to the gene which encodes the UGT8 protein, also referred to UDP glycosyltransferase 8. The human homolog of UGT8 is encoded by the human gene identified as EntrezGene #7368 and is located at chromosomal location 4q26. The protein encoded by human UGT8 has the Protein Accession # Q16880.2, however other protein accession numbers may also be assigned to this protein. UGT8 may also include other isoforms and/or splice variants. Other mammalian UGT8 homologs may include but are not limited to: *Rattus norvegicus* (EntrezGene #50555), *Mus musculus* (EntrezGene #22239).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. Eukaryotic basal promoters typically, though not necessarily, contain a TATA-box and/or a CAAT box. A 'UGT8 basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 3 or 4.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. A 'UGT8 regulatory element', in the context of the present invention and as used herein, is a nucleic acid compound having a sequence with at least 65%, at least 70%, at least 80%, at least 85%, at least 90%, at least 95%, or at least 99% similarity to any one of SEQ ID NO: 5-10. The present invention provides, in certain embodiments as described herein, different promoters of the UGT8 gene. In some embodiments, the UGT8 promoter comprises one or more UGT8 regulatory elements operably linked to a UGT8 basal promoter.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are selected from an endogenous full length promoter for a gene, usually in such a fashion as to reduce the overall size of the promoter compared to the native sequence. For example, after identification of critical promoter elements, using one or more of various techniques, the native sequences that intervene between identified elements may be partially or completely removed. Other non-native sequences may optionally be inserted between the identified promoter elements. Promoter sequences such as enhancer elements may have an orientation that is different from the native orientation—for example, a promoter element may be inverted, or reversed, from its native orientation. Alternatively, selecting a minimal basal promoter that is sufficient to drive expression in particular cells or tissues may also be desirable. Since promoter elements that impact expression patterns are known to be distributed over varying distances of the proximal and/or distal endogenous promoter, it is a non-trivial task to identify a mini-promoter comprising a minimal basal promoter and optional regulatory regions that will adequately express in the desired cell or tissue types. A mini-promoter may provide certain advantages over native promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters are apparent to one of skill in the art. In some embodiments of the invention, there are thus provided novel UGT8 mini-promoters comprising a UGT8 regulatory element operably linked in a non-native conformation to a UGT8 basal promoter. In general the spacing between the UGT8 regulatory element and the UGT8 basal promoter is not more than about 15 KB, generally not more than about 10 KB, usually not more than about 1 KB, more often not more than about 500 nt, and may be not more than about 100 nt, down to a direct joining of the two sequences. In other embodiments, there is provided a minimal UGT8 basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 KB or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to downregulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson, Plaehn et al. 1996; Jasin, Moynahan et al. 1996). The HPRT gene has additional advantages as a genomic targeting sequence, for instance its concomitant use as a selectable marker system. Other genomic targeting sequences that may be useful in the present invention are described in the art, for instance (Jasin, Moynahan et al. 1996; van der Weyden, Adams et al. 2002). The genomic targeting signals as described herein are useful in certain embodiments of the present invention.

Introduction of nucleic acids or expression vectors into cells may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

In certain embodiments of the invention, there are provided methods of treatment using the nucleic acids or expression vectors, for instance for gene therapy applications. The nucleic acids or expression vectors of the present invention may be administered in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, intraocular, topical or oral administration. An excipient may include sterile aqueous solutions or dispersions for extemporaneous preparation of sterile injectable solutions or dispersion. Use of such media for preparation of medicaments is known in the art.

The nucleic acids or expression vectors of the present invention may be administered to a subject using a viral delivery system. For instance, the nucleic acids may be inserted into a viral vector using well known recombinant techniques. The subsequent viral vector may then be packaged into a virus, such as adenovirus, lentivirus, attenuated virus, adeno-associated virus (AAV), and the like. Viral delivery for gene therapy applications is well known in the art. There exist a variety of options for viruses suitable for such delivery, which may also involve selecting an appropriate viral serotype for delivery and expression in an appropriate tissue.

Compositions or compounds according to some embodiments of the invention may be administered in any of a variety of known routes. Examples of methods that may be suitable for the administration of a compound include orally, intravenous, inhalation, intramuscular, subcutaneous, topical, intraperitoneal, intra-ocular, intra-rectal or intra-vaginal suppository, sublingual, and the like. The compounds of the present invention may be administered as a sterile aqueous solution, or may be administered in a fat-soluble excipient, or in another solution, suspension, patch, tablet or paste format as is appropriate. A composition comprising the compounds of the invention may be formulated for administration by inhalation. For instance, a compound may be combined with an excipient to allow dispersion in an aerosol. Examples of inhalation formulations will be known to those skilled in the art. Other agents may be included in combination with the compounds of the present invention to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments of the invention may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the compounds of the invention to the target tissue or cell in which protein expression. It is also understood that it may be desirable to target the compounds of the invention to a desired tissue or cell type. The compounds of the invention may thus be coupled to a targeting moiety. The compounds of the invention may be coupled to a cell uptake moiety. The targeting moiety may also function as the cell uptake moiety.

UGT8 Mini-promoters

The present invention herein provides novel UGT8 mini-promoter sequences which are capable of effecting transcriptional expression in a spatial and temporal fashion in the brain and/or eye. Certain UGT8 mini-promoters of the invention comprise minimal UGT8 promoter elements joined in a non-native configuration, thus providing advantageous characteristics. Also provided are novel expression vector compositions comprising UGT8 mini-promoters which allow consistent specific spatiotemporal transcription of expression sequences. Also provided are novel methods utilizing these UGT8 mini-promoters and expression vectors.

The UGT8 promoters of the invention, as described herein, are referred to as 'mini-promoters' to reflect the fact that the mini-promoters comprise minimal UGT8 promoter elements sufficient to drive expression, and that may also be joined by non-native sequences. In this context, the native intervening sequences may have been partially or completely removed, and optionally may have been replaced with non-native sequences. Furthermore, the natural spatial arrangement of elements may be altered, such that downstream promoter elements (in natural conformation) are moved upstream (in non-native conformation). In such a fashion, the natural spacing of the promoter elements, for instance one or more human UGT8 regulatory elements corresponding to one or more of SEQ ID NO: 5-10, and the human UGT8 basal promoter element corresponding to SEQ ID NO: 3 or 4, or sequences with substantial functional and/or sequence equivalence, is altered. Additionally, the orientation of the different promoter elements may be altered—for instance the regulatory element corresponding to one or more of SEQ ID NO: 5-10 may be inverted relative to the basal promoter element corresponding to SEQ ID NO: 3 or 4. An advantage of such non-native mini-promoters is that the removal of native intervening sequences reduces the size of the mini-promoter while maintaining the functional activity of the promoter, thus improving the utility of the mini-promoter for various applications. Furthermore, the inversion of an enhancer/promoter element may allow retention of the enhancer properties without causing alternate promoter activity.

The inventors have demonstrated, as illustrated in the non-limiting Working Examples, that a human UGT8 mini-promoter having a sequence corresponding to SEQ ID NO: 1 (also referred to in the Working Examples as Ple240), and which is comprised of 3 human UGT8 regulatory elements (corresponding to SEQ ID NOs: 5, 6 and 7) operably linked in a non-native conformation to a human UGT8 basal promoter having a nucleic acid sequence corresponding to SEQ ID NO: 3, is capable of directing expression of an expressible sequence which is operably linked downstream of the UGT8 promoter in specific cell types in different regions of the brain and/or eye. The UGT8 regulatory elements (SEQ ID NO: 5-7) and UGT8 basal promoter element (SEQ ID NO: 3) have sequences which are identical to those found in the human UGT8 gene. The inventors have further demonstrated, as illustrated in the non-limiting Working Examples, that a human UGT8 mini-promoter having a sequence corresponding to SEQ ID NO: 2 (also referred to in the Working Examples as Ple267), and which is comprised of 3 human UGT8 regulatory elements (corresponding to SEQ ID NO: 8-10) operably linked in a non-native conformation to a human UGT8 basal promoter having a nucleic acid sequence corresponding to SEQ ID NO: 4, is capable of directing expression of an expressible sequence which is operably linked downstream of the UGT8 promoter in specific cell types in different regions of the brain and/or eye. The UGT8 regulatory elements (SEQ ID NO: 8-10) and UGT8 basal promoter element (SEQ ID NO: 4) have sequences which are identical to those found in the human UGT8 gene. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate of an expressible sequence operably linked to a modified promoter sequence that is at least about 75% the transcription rate of the promoter sequence of SEQ ID NO: 1 or 2, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. The spacing of conserved sequences may be the same as the native spacing, or it may be different than the native spacing. The order of the conserved sequences may be the same as the native order or the sequences may be rearranged. Sequences set forth in SEQ ID NO: 1 or 2 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

In one embodiment of the invention, there is provided an isolated nucleic acid fragment comprising a UGT8 mini-promoter, wherein the UGT8 mini-promoter comprises one or more UGT8 regulatory elements operably linked in a non-native conformation to a UGT8 basal promoter. The UGT8 mini-promoter may have a nucleic acid sequence which is substantially similar in sequence and function to SEQ ID NO: 1 or 2. The UGT8 basal promoter may have a nucleic acid sequence which is substantially similar in sequence and function to SEQ ID NO: 3 or 4. The UGT8 regulatory element may have a nucleic acid sequence which is substantially similar in sequence and function to one or more of SEQ ID NO: 5-10, e.g. comprising one, two, three, four or five of the provided regulatory elements. The UGT8 mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

It is an object of the present invention to provide means of expressing a gene, protein, RNA interference molecule or the like in a cell, tissue or organ. As such, the inventors thus provide novel expression vectors comprising UGT8 mini-promoters which are capable of accomplishing this task. In one embodiment, there is provided an expression vector comprising a UGT8 mini-promoter, wherein the UGT8 mini-promoter comprises one or more UGT8 regulatory element operably linked in a non-native conformation to an UGT8 basal promoter. The UGT8 mini-promoter may have a nucleic acid sequence which is substantially similar in sequence and function to SEQ ID NO: 1 or 2. The UGT8 basal promoter may have a nucleic acid sequence which is substantially similar in sequence and function to SEQ ID NO: 3 or 4. The UGT8 regulatory element may have a nucleic acid sequence which is substantially similar in sequence and function to one or more of SEQ ID NO: 5-10. The UGT8 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT, e.g. human HPRT, mouse HPRT, etc.

The inventors have herein demonstrated that expression vectors comprising novel UGT8 mini-promoter elements are capable of directing transcription of an expression sequence in specific cell types, for instance in Muller glia cells in the retina (eye) or in neuronal cells in the brain. In one embodiment of the invention, there is thus provided a method for expressing a gene, protein, RNA interference molecule or the like in a cell, the method comprising introducing into the cell an expression vector comprising an UGT8 mini-promoter element, wherein the UGT8 mini-promoter element comprises one or more UGT8 regulatory element operably linked in a non-native conformation to a UGT8 basal promoter element. Cells of interest include, without limitation, cells of the peripheral or central nervous system and progenitors thereof, e.g. embryonic stem cells, neural stem cells, neurons, glial cells, astrocytes, microgial cells, etc; and/or cells in the eye and progenitors thereof, e.g. retinal cells, retinal Muller glial cells etc. The UGT8 mini-promoter may have a nucleic acid sequence which is substantially similar in sequence and function to SEQ ID NO: 1 or 2. The UGT8 basal promoter may have a nucleic acid sequence which is substantially similar in sequence and function to SEQ ID NO: 3 or 4. The UGT8 regulatory element may have a nucleic acid sequence which is substantially similar in sequence and function to one or more of SEQ ID NO: 5-10. The UGT8 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising an UGT8 mini-promoter element, wherein the UGT8 mini-promoter element comprises one or more UGT8 regulatory element operably linked in a non-native conformation to a UGT8 basal promoter element, and wherein the expressible sequence comprises a reporter gene. The UGT8 mini-promoter element may have a nucleic acid sequence substantially similar in sequence and function to SEQ ID NO: 1 or 2. The UGT8 basal promoter element may have a nucleic acid sequence substantially similar in sequence and function to SEQ ID NO: 3 or 4. The UGT8 regulatory element may have a nucleic acid sequence substantially similar in sequence and function to one or more of SEQ ID NO: 5-10. The inventors have demonstrated that expression vectors comprising certain human UGT8 promoter elements are capable of expression in specific regions of the brain and eye, most notably retinal Muller glial cells in the eye. In some embodiments, the cell is a peripheral or central nervous system cell or progenitors thereof, including, without limitation, embryonic stem cells, neural stem cells, glial cell, neuronal cells, astrocytes, and the like. In some embodiments, the cell is a cell of the eye and progenitors thereof, including without limitation retinal cells, retinal Muller glials cells, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In further embodiments of the invention, there is provided a method for monitoring or tracking the development or maturation of a cell, the method comprising: 1) introducing into the cell a expression vector comprising an UGT8 mini-promoter element operably linked to an expressible sequence, wherein the UGT8 mini-promoter element comprises one or more UGT8 regulatory elements operably linked in a non-native conformation to an UGT8 basal promoter element, and wherein the expressible sequence comprises a reporter gene; and 2) detecting the expression of the reporter gene in the cell of in progeny of the cell as a means of determining the lineage, identity or developmental state of the cell or cell progeny. The UGT8 mini-promoter element may have a nucleic acid sequence substantially similar in sequence and function to SEQ ID NO: 1 or 2. The UGT8 basal promoter element may have a nucleic acid sequence substantially similar in sequence and function to SEQ ID NO: 3 or 4. The UGT8 regulatory element may have a nucleic acid sequence substantially similar in sequence and function to one or more of SEQ ID NO: 5-10 and/or 6. In such a fashion, one may be able to follow the development of a parent cell as it differentiates into more mature cells. As an example, one could introduce an expression vector comprising the aforementioned UGT8 mini-promoter elements into a pluripotent stem cell, monitor the expression of the reporter gene that is being expressed by the UGT8 promoter elements during the maturation and differentiation of the stem cell and thus determine the state of maturation, for instance in the differentiation of the pluripotent stem cell into a specific brain or retinal cell type. The inventors have demonstrated that the UGT8 mini-promoter elements described herein direct transcriptional expression in certain brain and retinal cell types, and so detection of reporter gene expression in a cell would thus be indicative of the cellular identity of the cell as being a certain type of brain or retinal cell.

The inventors have herein demonstrated that certain UGT8 mini-promoter elements of the present invention are capable of driving expression in retinal Muller glial cells. This surprising expression pattern provides additional methods of use for these mini-promoter elements. For instance, the UGT8 mini-promoters of the present invention can be utilized in a gene therapy or cell therapy application wherein the UGT8 mini-promoters are utilized to drive expression of a therapeutic or beneficial compound, such as a protein, in retinal Muller glial cells. In such a way, the therapeutic or beneficial compound can be useful for a disease or condition that involves such retinal cells, or which may be improved by expression of the therapeutic or beneficial compound in those cells. In certain embodiments of the invention, there is thus provided a method of treatment of a subject having a disease or condition of the eye, the method comprising administering to the subject a therapeutically effective dose of a composition comprising an UGT8 mini-promoter element, wherein the UGT8 mini-promoter element comprises one or more UGT8 regulatory element operably linked in a non-native conformation to an UGT8 basal promoter element. The UGT8 mini-promoter element may have a nucleic acid sequence substantially similar in sequence and function to SEQ ID NO: 1 or 2. The UGT8 basal promoter element may have a nucleic acid sequence substantially similar in sequence and function to SEQ ID NO: 3 or 4. The UGT8 regulatory element may have a nucleic acid sequence substantially similar in sequence and function to one or more of SEQ ID NO: 5-10. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy. The therapeutic or beneficial compound may be a light-sensitive compound, for instance rhodopsin, channel rhodopsin, etc.

The inventors herein further describe the present invention by way of the following non-limiting examples:

WORKING EXAMPLES

General Methods
Virus Generation and Analysis
Virus Production

The Ple240 and Ple267 (UGT8) MiniPromoters were generated by direct synthesis by DNA2.0 (Menlo Park, Calif., USA) (SEQ ID NO: 1 or 2). Promoter elements were cloned into the pEMS1980 backbone, containing the iCre reporter, using AvrII and AscI restriction enzymes. One µg of pEMS1981 plasmid containing either the Ple240 or Ple267 MiniPromoter was prepared by miniprep and sent to the Vector Core at the University of Pennsylvania (Philadelphia, Pa., USA) to be made into AAV9 serotype virus.

Virus Injection

B6-Gt(ROSA26)$^{tm1Sor}$ females were crossed to 129-Gt(ROSA26)$^{tm1Sor}$ to yield hybrid F1 homozygous pups for injecting virus. Plug checks were performed on the females such that the day of birth could be accurately estimated. P0 pups were used for virus injections. If the female gave birth in the morning, virus was injected in the afternoon. If she gave birth in the afternoon, virus was injected the next morning. A standard injection into the superficial temporal vein of a newborn pup was performed using $1 \times 10^{13}$ GC/mL (genome copies per milliliter) virus in a total volume of 50 µL (in PBS) with a 30 gauge needle and a 1 cc syringe. After injections, pups were tattooed for identification and returned to their cage.

Harvesting of Animals

Virus-injected mice were harvested at P21 or P56 (postnatal day 21 or 56). Animals were given a lethal dose of avertin injected intraperitoneally. Thereafter perfusion with 1×PBS for 2 minutes and 4% PFA/PBS for 8 minutes was performed. Tissues were harvested and post-fixed for 1 hour at 4° C. The tissues were then stored in 0.02% Azide/PBS at 4° C.

Histology

Tissues were cryoprotected in 30% sucrose/PBS overnight at 4° C. After embedment in OCT the following day, 20 µm sections were directly mounted onto slides. For X-gal staining, tissues were rinsed in PBS and Triton-X/PBS and stained in 0.1% X-gal solution overnight at 30-35° C. After staining sections were rinsed and counterstained with neutral red, dehydrated and mounted with coverslips. For co-labeling of X-gal with markers using immunohistochemistry, standard IHC procedure was followed and the X-gal stain was performed either prior to primary antibody incubation or between primary and secondary antibodies, depending on the strength of the X-gal stain. X-gal stains blue any cells that have recombined the Gt(ROSA26)$^{tm1Sor}$ locus due to iCre recombinase activity and thus expressing the β-galactosidase protein.

Knock-in Mouse Generation and Analysis
Expression Vector

The nucleic acid fragment corresponding to (SEQ ID NO: 1 or 2) was inserted into the multiple cloning site of pEMS1313 (driving the lacZ or EGFP reporter) to produce the expression vector (Ple240 or Ple267) used in the experiments.

Derivation of mEMS1202 Embryonic Stem Cells

Blastocysts were obtained from natural mating of B6-Hprt$^{b-m3}$ homozygous females to 129-ROSA26 heterozygous males at 3.5 dpc. Blastocysts were flushed from uterine horns as per (Hogan, Beddington et al. 1994), cultured in EmbryoMax® KSOM with 1/2 Amino Acids, Glucose and Phenol Red (Cat # MR-121, Millipore/Chermicon, Temecula, Calif.) for 3-5 h, and then transferred onto mitomycin C (mitC; Cat#M4287, Sigma, Oakville, ON) mitotically inactivated B6-Hprtb-m3, B6129F1, or 129 mouse embryonic feeders (MEFs) derived from 13.5-day post-coital embryos (Ponchio, Duma et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer). Blastocysts were cultured as per (Cheng, Dutra et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well-developed ICM (inner cell mass) were treated with 20 µl 0.25% trypsin-EDTA (Invitrogen, Burlington, ON) for 5 min at 37° C., triturated with a 200 µl Pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml. Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON), 1000 U ESGRO-LIF (Millipore, ESG1107) and 0.01% β-mercaptoethanol (Sigma, Oakville, ON)) in 25%, 50%, 75% proportions (respectively) to adapt the cells to FBS-containing media. On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sortm1Sor and WT alleles and Hprtb-m3 and WT alleles. B6129F1-Gt(ROSA) 26Sor$^{tm1Sor/+}$, Hprt$^{b-m3}$/Y (mEMS1204 series) and B6129F1-Gt(ROSA)26Sor$^{tm1Sor+/+}$, Hprt$^{b-m3}$/Y (mEMS1202 series) cell lines were identified.

Knock-in at the Hprt Locus

The expression vector plasmid DNA was purified with Qiagen Maxi Kit (Qiagen, Mississauga, ON), resuspended in 10:1 Tris-EDTA (TE, pH7.0) buffer, and linearized with I-SceI (New England Biolabs, Pickering, ON). Linearized plasmid DNA was resuspended in 85 µl of TE (10:0.1) to a final concentration of 187.5 ng/µl. Ple240 or Ple267 was targeted in our in-house derived mEMS1202 cell line. ESCs were grown to confluence on 4-6 T75 flasks of mitC treated Hprtb-m3 mouse embryonic feeders (MEFs) in FBS-ESC media. ESCs (1.7-2.5×107) in 720 µl 1× PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml per 100 mm dish. 24-36 h post-electroporation, correctly targeted homologous recombinants were selected for using HAT media (FBS-ESC media containing 1× HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3rd day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of Knock-in Mice

Chimeric mice from targeted ESCs were generated by microinjection (Hogan, Beddington et al. 1994) into E3.5 blastocysts followed by implantation into the uterine horns of 2.5 day pseudopregnant ICR females. Chimeras were identified and coat color chimerism determined as outlined below.

Male chimeras derived from the E14TG2a cell lines were mated with B6 or B6-Alb females, and germline transmission was identified in the former case by the transmission of the dominant Aw (white bellied agouti) allele, making the progeny appear brown with a cream belly, or in the latter case by the combination of A$^w$ and Tyr$^{c-ch}$ (chinchilla), making the progeny appear golden. Non-germline progeny from the cross to B6 were homozygous for the recessive a (nonagouti) allele and appeared black, whereas non-germline progeny from the cross to B6-Alb were homozygous for the recessive Tyr$^{c-2J}$ (albino 2 Jackson) allele and appeared white.

Male chimeras derived from the cell lines were mated with B6-Alb females, and germline transmission identified by the presence of the dominant Tyr$^+$ (tyrosinase; wild type) and the Aw (white bellied agouti) or a (nonagouti) alleles making the progeny appear brown with a cream belly or black, respectively. Non-germline progeny were homozygous for the recessive Tyr$^{c-2J}$ (albino 2 Jackson) allele and appeared white. All germline female offspring carry the knock-in X Chromosome and were mated with B6 males.

N2 offspring were analyzed for the presence of the KI allele by PCR.

Reporter Gene Detection

Adult male hemizygous MiniPromoter and age matched control mice were perfused with 4% paraformaldehyde (PFA) as previously described (Young, Berry et al. 2002). Whole brains and eyes were dissected out and post-perfusion immersion fixed with PFA for 2 hours at 4° C. The brains were sectioned using a coronal or sagittal brain mold (Electron Microscopy Sciences) at 1 mm and sections were placed in 12-well tissue culture plates. One whole eye and one half-cut eye, using a razorblade, was also placed in the plate. LacZ expression was detected by using 5-bromo-4-chloro-3-indolyl-β-D-galactopyranoside (X-Gal) as the substrate. The X-Gal staining solution contained the following: 1.0 mg/ml X-Gal, 2 mM potassium ferricyanide, 2 mM potassium ferrocyanide, and 40 mM MgCl$_2$ in PBS. In brief, brain sections were rinsed with phosphate buffered saline (PBS), then incubated with X-Gal (Boeringer Mannheim, Indianapolis, Ind.) at 37° C., usually overnight. After staining the tissue was rinsed with PBS and moved into PBS containing 0.02% azide for storage. Eyes were further processed by post-fixing with 4% PFA for 2 hours at room temperature. After fixation, eyes were rinsed with PBS and cryoprotected in 25% sucrose-PBS at 4° C. overnight. Eyes were removed from the solution and blotted with a KimWipe before embedment in Optimal Cutting Temperature (OCT) alongside positive and negative controls. 12 µm sections were taken using a Microm HM 550 cryostat and directly mounted onto SuperFrost Plus microscope slides. Bright field images were taken on a Leica MZ125 dissecting microscope and photographed using an Olympus Coolsnap cf color camera with the ImagePro software package.

Example 1

Selection of UGT8 Mini-promoter Elements

The Ple240 construct was designed based on the UGT8 gene. It combines a basal promoter (SEQ ID NO: 3) along with three upstream conserved elements with putative regulatory function segment 1 (SEQ ID NO: 5), segment 2 (SEQ ID NO: 6), and segment 3 (SEQ ID NO: 7). The Ple267 construct was designed based on the UGT8 gene, and includes improvements made to the previously described Ple240 design. The construct includes a basal promoter (SEQ ID NO: 4) along with three upstream conserved elements with putative regulatory function segment 1 (SEQ ID NO: 8), segment 2 (SEQ ID NO: 9), and segment 3 (SEQ ID NO: 10).

Example 2

Expression of Reporter in Brain and Eye by Ple240 Mini-promoter

The Ple240 construct was subsequently tested as a single-copy site-specific knock-in at the mouse Hprt locus as previously published (Yang et al. 2009; Portales-Casamar et al. 2010; de Leeuw et al. 2014). Mice were harvested by cardiac perfusion, sectioned, and stained with the X-gal substrate, which leaves a blue product after enzymatic cleavage by beta-galactosidase. In the brain, showed strong fiber-tract associated staining in all parts of the brain, with cortex layer IV strongly positive and in thalamic intralaminar and anterior nuclei groups. The olfactory bulbs have clear glomeruli staining and ventricles are also lined with positive cells. In the spinal cord, Ple240 is expressed strongly and predominantly along spinal nerve cord bundles with weaker expression in the central spinal cord tissue and in dorsal root ganglia.

Additionally, the eye showed staining throughout all layers, which may be indicative of Müller glia cells. Eye expression for endogenous UGT8 has not been previously reported.

Example 3

Expression of Reporter in Brain by Ple267 Mini-promoter

The Ple267 construct was subsequently tested in ssAAV9 driving the icre reporter (Cre recombinase), resulting in vEMS40. Mice were injected intravenously with virus at post-natal day 0 (P0) (method of (Foust et al. 2009)), and expression analyzed at P21 and P56 via recombination of the reporter locus Gt(ROSA26)SortmSor1 (Soriano 1999). Once recombined, this locus expresses the β-galactosidase (lacZ gene) enzyme. Mice were harvested by cardiac perfusion, sectioned, and stained with the X-gal substrate, which leaves a blue product after enzymatic cleavage by beta-galactosidase. Staining in the brain (e.g. cortex and corpus callosum) is suggestive of oligodendrocytes. Similarly, white matter tracts are often positive. The spinal cord has extensive staining along nerve fiber bundles as well. These results suggest an oligodendroglial cell type.

LIST OF SEQUENCES

SEQ ID NO: 1; Ple240 human UGT8 mini-promoter element
SEQ ID NO: 2; Ple267 human UGT8 Mini-Promoter
SEQ ID NO: 3; UGT8 Basal Promoter element #1
SEQ ID NO: 4; UGT8 Basal Promoter element #2
SEQ ID NO: 5; UGT8 Regulatory Element #1
SEQ ID NO: 6; UGT8 Regulatory Element #2
SEQ ID NO: 7; UGT8 Regulatory Element #3
SEQ ID NO: 8; UGT8 Regulatory Element #4
SEQ ID NO: 9; UGT8 Regulatory Element #5
SEQ ID NO: 10; UGT8 Regulatory Element #6

What is claimed is:

1. An isolated polynucleotide comprising a UGT8 mini-promoter wherein the UGT8 mini-promoter comprises at least one UGT8 regulatory element with at least 95% sequence identity to SEQ ID NO: 8, 9 or 10 operably joined to an UGT8 basal promoter with at least 95% sequence identity to SEQ ID NO: 4, wherein the spacing between the UGT8 regulatory element and the UGT8 basal promoter is not more than 500 nucleotides (nt).

2. The isolated polynucleotide of claim 1, comprising 2 or more UGT8 regulatory elements.

3. The isolated polynucleotide of claim 1, comprising 3 or more UGT8 regulatory elements.

4. The isolated polynucleotide of claim 1 wherein the UGT8 mini-promoter has at least 95% sequence identity to SEQ ID NO: 2.

5. The isolated polynucleotide of claim 1, comprising a UGT8 mini-promoter with at least 99% sequence identity to SEQ ID NO: 2.

6. The isolated polynucleotide of claim 1, operably linked to an expressible sequence.

7. A vector comprising the isolated polynucleotide of claim 1.

8. An isolated cell comprising the vector of claim 7.

9. The cell of claim 8, wherein the vector is stably integrated into the genome of the cell.

10. The cell of claim 8, wherein the cell is a stem cell, a retinal cell, a brain or a glial cell.

* * * * *

```
SEQUENCE LISTING

<160> NUMBER OF SEQ ID NOS: 10

<210> SEQ ID NO 1
<211> LENGTH: 3792
<212> TYPE: DNA
<213> ORGANISM: H. sapiens

<400> SEQUENCE: 1
aaaactgaat acatttcgtc aaaatacaaa agtaaaagta tttctaggac ttgaaaggtg      60
agctaaatga tgagaacaca tggacacata caagtttacc tatataatga atttgcacat     120
gtaccactga acttaaaagt tttttaaaag tatttctagg aaagtacaaa ctatttaaaa     180
tcattagtta gttttgaact aaaatccttt aaaaatatac aacaaaaaag gtagtttcca     240
gatgtccttt acactgttac tgagaatgta aaatgtcttt cattaatttg gattctttaa     300
acattcctct atgatcatat ttaagtgtga aattttactc cctattgttg tagataatct     360
tttagtcagg taatgaatag cacatggtac agaaaaacat atacatatac attttcattt     420 cagctttttct gaagccccat tgtttatttc aggctgcttt actgagactc cttgcactaa    480
acgcctctgg ttgcattcca ctcaagacaa aggcatattt tagggatgta cctctgacaa     540
agaggtattt atggaccagg aatcagactt tggacaaatg ggcatttcat tataacacag     600
cctaattgtt aaagctctta ttgaaaagaa taaaaatttc attagtcatc acaggaactc     660
```

```
agcacaaact cctcctcctt ttccccacaa tgcacagaaa gaatggcagc tttaagctta    720
tcattgaaca ttttgaaggc tttggtcctt ccttccttt gttccacttg cactaagaag    780
tattttagta acaattgtga ataactgtg gtaataattt taacgaaatt ttataaatgt    840
aattgttaaa cacatctaaa tacacggagc agtcagggag gtgggacgag caggtcattc    900
ctcctaacct cacgacatag tcatgctaaa tcttctgctc ctaagtgcag cacactgggg    960
gaaaggaaag gccaaagag ggagggtcat caactgcaga gttccacggg gttccaggtg   1020
attgcaggtt ataaagcagc ttggtgcctg tataggctta gtaaatcaag aagtgatgtt   1080
aagataatgg aaacagcctg ctttgtataa atttgtttac tctgttctca ataggtaaca   1140
taatttgcat catatgctct atttatgaca cacctggatt cagaaatgag gtcattaagt   1200
tataaacttc atctggttct tttgtgaaaa atagacatca actattagcc cacttataaa   1260
ataacctgta taaattgtac cacctgtctc catgaagcct cttcaagtgt tcacaaatgt   1320
catttcagat gatatttcaa agttatgtat gtgtttcttc tgtaatatgt caagtttgca   1380
atgggttttt attgcaatgt ttctggttga ttaatgtgag atcaaacaga ccaagtccac   1440
agaaataatg agggaatttt aataccatac tccacattgg ctgaaacttt ctcactgcag   1500
gctatgctgt cccattcaac attctataaa ctaaagatga tagggagaat cttgtttaat   1560
ctgaatggga gcttgaagga tacattaaat atggaaaata tgcatccttc cttaaagaga   1620
agtagcaaat gttttcatta ttcatttatt caaccactta gccaataatg ttaacaatta   1680
aaggtgggag cattaaaaaa aggaaaagtg gggtggggcg gtgaaatgaa cctcactgat   1740
ttcttgcttt tatcatttca aactccaaaa gtgtatttca actattcata tgatgattga   1800
ataaacttgt tttacattat ggaacaccct tactgtgtag agctgtgaga aattcaataa   1860
tcagtattta atgtggacaa aaatagatag attagagaaa caataaacat ggacatatct   1920
acacataata tatactcctt ttctatccaa aaatctgaca aaaaccttac acaatggtca   1980
gtttacacca ttttaaggac aaggatgtgg tgaaacaatt ttaaacatt ttatataata   2040 aaagaaaaaa gttgttttaa ttgctaatga tcaagttttt accaagaatt tacatatgca   2100
tcatcaaaca gtagcttgaa actgaagctt gacctttgag aaataaagct tttaaagtaa   2160
atgtctaaat tctcttttct ttattatgtt acatttcatt tactttaggt tttctagtgc   2220
aatttaaata agaaataaat agagagtatg gtaatcaggt acaaaggctg tgaaaatatt   2280
ccctgcattt tgcacaggga atatgttcaa attcctaatc tgcaaagaag aaaagtgcat   2340
tttctttttt gaaatggcat ttgaagatct ctccatccat gaacattctt gagcatatgg   2400
attttacaat aacagcagtg tatattagtt ttttaattta tcattaactg ataacatata   2460
cagtaaaata taatttccgt tttccttatct aagggcagaa aatcccaacc tatttctgaa   2520
tctcactttg gaacaaggac agaatgacct gacatggcat ttttgatttc caacgtttaa   2580
acgcataacg tttgtgtgct atggaagcat cttagcttct ggaatttatg ctcgacacga   2640
aacataaaca ataaacaatt cagtccacgt tatatagaca tatctcatat atatatgaga   2700
tatatatata taaatatct tacgcacatg cacacttaga ctttctcggt tttcatgaaa   2760
ctcacaatct acctcaggcg ctcaaaggca ctcggcctct caggtctgag gcaccacaga   2820
gaggcttcct tgggcacagt tgcttgctgg tcaagacgcc aacttggcaa ggttatgctg   2880
ctggcaaagg cagattcgtc agaataaagt cgccacaggc tcaaccaggc aaatcatgaa   2940
tggccctttc agcaggagcc tgagaggagg gatgttattc agcccagcaa ccctatttac   3000
```

```
ttttttttcag atcccaaaa ctcgcgtttt ttaaggcttt ccgctacaag agagccaaaa    3060
ttgaagcctg ggttggcggc agtgcaggta cctgctcacc taagcatccc tcttttaatt    3120
ttcctaactc ctccacccca gagctcactg agccgccttg atgataaaag gcgggcacag    3180
ggactacgtg ggtggtggca gaaagggcgc gggacacgcc tcgcaaagag gaagagtgg     3240 gcggggccac gtgccggtgt cagagttcgc aactcgagcg cccagagggc tcgcgaaaag    3300
tcccagcctg caagccaacc gcgctcagcg gacgactggc cggatcccaa cgcgctgccc    3360
cttgcccagc ctgcgagcgc gtggtacgaa ggcgcgtctg catccatgcc ccagcccggg    3420
gagctggagg cgctcgcagt cagaggcgag tgatgctagg ctgagcgcgt ggcggcccgt    3480
gtcgtgcccc gctgagccaa gtgcggaagg gcagcggcgc gctccagctc tgctcgccgc    3540
gcgcagggcg gggggggctg gccgcccgct gggagctgcg gacgagcagg cgcgctgagg    3600
acccgaggga ggacacggtt aaagcattgc tatcaactgt gaacccagag agccctcctt    3660
agccaacacg ctaactccga agcctcccctt acgccccga accaccgaag gcggcgacac    3720
ctgattcagc gcacaaacac aggtcccttc tgtcccggat acaattacgc ggcagacaca    3780
cactcaaact cg                                                       3792

<210> SEQ ID NO 2
<211> LENGTH: 3014
<212> TYPE: DNA
<213> ORGANISM: H. sapiens

<400> SEQUENCE: 2
aaagtatttc taggaaagta caaactattt aaaatcatta gttagttttg aactaaaatc      60
ctttaaaaat atacaacaaa aaggtagtt tccagatgtc ctttacactg ttactgagaa     120
tgtaaaatgt ctttcattaa tttggattct ttaaacattc ctctatgatc atatttaagt     180
gtgaaatttt actccctatt gttgtagata atcttttagt caggtaatga atagcacatg     240
gtacagaaaa acatatacat atacattttc atttcagctt ttctgaagcc ccattgttta     300
tttcaggctg ctttactgag actccttgca ctaaacgcct ctggttgcat tccactcaag     360
acaaaggcat attttaggga tgtacctctg acaaagaggt atttatggac caggaatcag     420
actttggaca aatgggcatt tcattataac acagcctaat tgttaaagct cttattgaaa     480
agaataaaaa tttcattagt catcacagga actcagcaca aactcctcct cctttttcccc    540 acaatgcaca gaaagaatgg cagctttaag cttatcattg aacattttga aggctttggt     600
ccttccttcc ttttgttcca cttgcactaa gaagtatttt agtaacaatt gtgaaataac     660
tgtggtaata attttaacga aatttatata atgtatcttc tgctcctaag tgcagcacac     720
tgggggaaag gaaaggccaa aagagggagg gtcatcaact gcagagttcc acggggttcc     780
aggtgattgc aggttataaa gcagcttggt gcctgtatag gcttagtaaa tcaagaagtg     840
atgttaagat aatggaaaca gcctgctttg tataaatttg tttactctgt tctcaatagg     900
taacataatt tgcatcatat gctctatta tgacacacct ggattcagaa atgaggtcat     960
taagttataa acttcatctg gttcttttgt gaaaaataga catcaactat agcccacttt   1020
ataaaataac ctgtataaat tgtaccacct gtctccatga agcctcttca agtgttcaca   1080
acactgattt cttgcttta tcatttcaaa ctccaaaagt gtatttcaac tattcatatg   1140
atgattgaat aaacttgttt tacattatgg aacacccta ctgtgtagag ctgtgagaaa    1200
ttcaataatc agtatttaat gtggacaaaa atagatagat tagagaaaca ataaacatgg   1260
acatatctac acataatata tactccttt ctatccaaaa atctgacaaa aaccttacac    1320
```

```
aatggtcagt ttacaccatt ttaaggacaa ggatgtggtg aaacaatttt aaacattttt    1380
atataataaa agaaaaaagt tgttttaatt gctaatgatc aagttttac caagaattta     1440 catatgcatc atcaaacagt agcttgaaac tgaagcttga cctttgagaa ataaagcttt    1500
taaagtaaat gtctaaattc tcttttcttt attatgttac atttcattta ctttaggttt    1560
tctagtgcaa tttaaataag aaataaatag agagtatggt aatcaggtac aaaggctgtg    1620
aaaatattcc ctgcattttg cacagggaat atgttcaaat tcctaatctg caaagaagaa    1680
aagtgcattt tctttttga aatggcattt gaagatctct ccatccatga acattcttga     1740
gcatatggat tttacaataa cagcagtgta tattagtttt ttaatttatc attaactgat    1800
aacatataca gtaaaatata atttccgttt tcttatctaa gggcagaaaa tcccaaccta    1860
tttctgaatc tcactttgga acaaggacag aatgacctga catggcatttt ttgatttcca   1920 acgtttaaac gcataacgtt tgtgtgctat ggaagcatct tagcttctgg aatttatgct    1980
cgacacgaaa cataaacaat aaacaattca gtccacgtta tatagacata tctcatatat    2040
atatgagata tatatatata aaatatctta cgcacatgca cacttagact ttctcggttt    2100
tcatgaaact cacaatctac ctcaggcgct caaaggcact cggcctctca ggtctgaggc    2160
accacagaga ggcttccttg ggcacagttg cttgctggtc aagacgccaa cttggcaagg    2220
ttatgctgct ggcaaaggca gattcgtcag aataaagtcg ccacaggctc aaccaggcaa    2280
atcatgaatg gccctttcag caggagcctg agaggaggga tgttattcag cccagcaacc    2340
ctatttactt tttttcagga tccccaaact cgcgtttttt aaggctttcc gctacagcac    2400
agggactacg tgggtggtgg cagaaagggc gcgggacacg cctcgcaaag agggaagagt    2460
gggcggggcc acgtgccggt gtcagagttc gcaactcgag cgcccagagg gctcgcgaaa    2520
agtcccagcc tgcaagccaa ccgcgctcag cggacgactg gccggatccc aacgcgctgc    2580
cccttgccca gctgcgagc gcgtggtacg aaggcgcgtc tgcatccatg ccccagcccg     2640
gggagctgga ggcgctcgca gtcagaggcg agtgatgcta ggctgagcgc gtggcggccc    2700
gtgtcgtgcc ccgctgagcc aagtgcggaa gggcagcggc gcgctccagc tctgctcgcc    2760
gcgcgcaggg cgggggggc tggccgcccg ctggagctg cggacgagca ggcgcgctga      2820
ggacccgagg gaggacacgg ttaaagcatt gctatcaact gtgaacccag agagccctcc    2880
ttagccaaca cgctaactcc gaagcctccc ttacgccccc gaaccaccga aggcggcgac    2940
acctgattca gcgcacaaac acaggtccct tctgtcccgg atacaattac gcggcagaca    3000
cacactcaaa ctcg                                                       3014
```

<210> SEQ ID NO 3
<211> LENGTH: 654
<212> TYPE: DNA
<213> ORGANISM: H. sapiens

<400> SEQUENCE: 3

```
cagagctcac tgagccgcct tgatgataaa aggcgggcac agggactacg tgggtggtgg      60
cagaaagggc gcgggacacg cctcgcaaag agggaagagt gggcggggcc acgtgccggt     120
gtcagagttc gcaactcgag cgcccagagg gctcgcgaaa agtcccagcc tgcaagccaa     180
ccgcgctcag cggacgactg gccggatccc aacgcgctgc cccttgccca gctgcgagc     240 gcgtggtacg aaggcgcgtc tgcatccatg ccccagcccg gggagctgga ggcgctcgca     300
gtcagaggcg agtgatgcta ggctgagcgc gtggcggccc gtgtcgtgcc ccgctgagcc     360
```

| | | |
|---|---|---|
| aagtgcggaa gggcagcggc gcgctccagc tctgctcgcc gcgcgcaggg cggggggggc | 420 | |
| tggccgcccg ctgggagctg cggacgagca ggcgcgctga ggacccgagg gaggacacgg | 480 | |
| ttaaagcatt gctatcaact gtgaacccag agagccctcc ttagccaaca cgctaactcc | 540 | |
| gaagcctccc ttacgccccc gaaccaccga aggcggcgac acctgattca gcgcacaaac | 600 | |
| acaggtccct tctgtcccgg atacaattac gcggcagaca cacactcaaa ctcg | 654 | |

<210> SEQ ID NO 4
<211> LENGTH: 618
<212> TYPE: DNA
<213> ORGANISM: H. sapiens

<400> SEQUENCE: 4

| | | |
|---|---|---|
| gcacagggac tacgtgggtg gtggcagaaa gggcgcggga cacgcctcgc aaagagggaa | 60 | |
| gagtgggcgg ggccacgtgc cggtgtcaga gttcgcaact cgagcgccca gagggctcgc | 120 | |
| gaaaagtccc agcctgcaag ccaaccgcgc tcagcggacg actggccgga tcccaacgcg | 180 | |
| ctgcccttg cccagcctgc gagcgcgtgg tacgaaggcg cgtctgcatc catgcccag | 240 | |
| cccggggagc tggaggcgct cgcagtcaga ggcgagtgat gctaggctga gcgcgtggcg | 300 | |
| gcccgtgtcg tgccccgctg agccaagtgc ggaagggcag cggcgcgctc cagctctgct | 360 | |
| cgccgcgcgc agggcggggg gggctggccg cccgctggga gctgcggacg agcaggcgcg | 420 | |
| ctgaggaccc gagggaggac acggttaaag cattgctatc aactgtgaac ccagagagcc | 480 | |
| ctccttagcc aacacgctaa ctccgaagcc tcccttacgc ccccgaacca ccgaaggcgg | 540 | |
| cgacacctga ttcagcgcac aaacacaggt cccttctgtc ccggatacaa ttacgcggca | 600 | |
| gacacacact caaactcg | 618 | |

<210> SEQ ID NO 5
<211> LENGTH: 850
<212> TYPE: DNA
<213> ORGANISM: H. sapiens

<400> SEQUENCE: 5

| | | |
|---|---|---|
| aaaactgaat acatttcgtc aaaatacaaa agtaaaagta tttctaggac ttgaaaggtg | 60 | |
| agctaaatga tgagaacaca tggacacata caagtttacc tatataatga atttgcacat | 120 | |
| gtaccactga acttaaaagt ttttttaaaag tatttctagg aaagtacaaa ctatttaaaa | 180 | |
| tcattagtta gttttgaact aaaatccttt aaaaatatac aacaaaaaag gtagtttcca | 240 | |
| gatgtccttt acactgttac tgagaatgta aaatgtcttt cattaatttg gattctttaa | 300 | |
| acattcctct atgatcatat ttaagtgtga aattttactc cctattgttg tagataatct | 360 | |
| tttagtcagg taatgaatag cacatggtac agaaaaacat atacatatac attttcattt | 420 | |
| cagcttttct gaagccccat tgtttatttc aggctgcttt actgagactc cttgcactaa | 480 | |
| acgcctctgg ttgcattcca ctcaagacaa aggcatattt tagggatgta cctctgacaa | 540 | |
| agaggtattt atggaccagg aatcagactt tggacaaatg ggcatttcat tataacacag | 600 | |
| cctaattgtt aaagctctta ttgaaaagaa taaaatttc attagtcatc acaggaactc | 660 | |
| agcacaaact cctcctcctt ttccccacaa tgcacagaaa gaatggcagc tttaagctta | 720 | |
| tcattgaaca ttttgaaggc tttggtcctt ccttcctttt gttccacttg cactaagaag | 780 | |
| tattttagta acaattgtga ataactgtg gtaataattt taacgaaatt ttataaatgt | 840 | |
| aattgttaaa | 850 | |

-continued

```
<210> SEQ ID NO 6
<211> LENGTH: 583
<212> TYPE: DNA
<213> ORGANISM: H. sapiens

<400> SEQUENCE: 6
cacatctaaa tacacggagc agtcagggag gtgggacgag caggtcattc ctcctaacct      60
cacgacatag tcatgctaaa tcttctgctc ctaagtgcag cacactgggg gaaaggaaag    120
gccaaaagag ggagggtcat caactgcaga gttccacggg gttccaggtg attgcaggtt    180
ataaagcagc ttggtgcctg tataggctta gtaaatcaag aagtgatgtt aagataatgg    240
aaacagcctg ctttgtataa atttgtttac tctgttctca ataggtaaca taatttgcat    300
catatgctct atttatgaca cacctggatt cagaaatgag gtcattaagt tataaacttc    360
atctggttct tttgtgaaaa atagacatca actattagcc cacttataaa ataacctgta    420
taaattgtac cacctgtctc catgaagcct cttcaagtgt tcacaaatgt catttcagat    480
gatatttcaa agttatgtat gtgtttcttc tgtaatatgt caagtttgca atgggttttt    540
attgcaatgt ttctggttga ttaatgtgag atcaaacaga cca                      583

<210> SEQ ID NO 7
<211> LENGTH: 1705
<212> TYPE: DNA
<213> ORGANISM: H. sapiens

<400> SEQUENCE: 7
agtccacaga aataatgagg gaattttaat accatactcc acattggctg aaactttctc      60
actgcaggct atgctgtccc attcaacatt ctataaacta aagatgatag ggagaatctt    120
gtttaatctg aatgggagct tgaaggatac attaaatatg gaaaatatgc atccttcctt    180
aaagagaagt agcaaatgtt ttcattattc atttattcaa ccacttagcc aataatgtta    240
acaattaaag gtgggagcat taaaaaaagg aaaagtgggg tggggcggtg aaatgaacct    300
cactgatttc ttgcttttat catttcaaac tccaaaagtg tatttcaact attcatatga    360
tgattgaata aacttgtttt acattatgga acacccttac tgtgtagagc tgtgagaaat    420
tcaataatca gtatttaatg tggacaaaaa tagatagatt agagaaacaa taaacatgga    480
catatctaca cataatatat actccttttc tatccaaaaa tctgacaaaa accttacaca    540
atggtcagtt tacaccattt taaggacaag gatgtggtga acaattttta acatttttta    600
tataataaaa gaaaaagtt gttttaattg ctaatgatca gttttttacc aagaatttac    660
atatgcatca tcaaacagta gcttgaaact gaagcttgac ctttgagaaa taaagctttt    720
aaagtaaatg tctaaattct cttttcttta ttatgttaca tttcatttac tttaggtttt    780
ctagtgcaat ttaaataaga aataaataga gagtatggta atcaggtaca aaggctgtga    840
aaatattccc tgcattttgc acagggaata tgttcaaatt cctaatctgc aaagaagaaa    900
agtgcatttt ctttttgaa atggcatttg aagatctctc catccatgaa cattcttgag    960
catatggatt ttacaataac agcagtgtat attagttttt taatttatca ttaactgata   1020
acatatacag taaatataa tttccgtttt cttatctaag ggcagaaaat cccaacctat   1080
ttctgaatct cactttggaa caaggacaga atgacctgac atggcatttt tgatttccaa   1140
cgttaaaacg cataacgttt gtgtgctatg aagcatctt agcttctgga atttatgctc   1200
gacacgaaac ataaacaata aacaattcag tccacgttat atagacatat ctcatatata   1260
tatgagatat atatatataa aatatcttac gcacatgcac acttagactt tctcggtttt   1320
```

```
catgaaactc acaatctacc tcaggcgctc aaaggcactc ggcctctcag gtctgaggca   1380
ccacagagag gcttccttgg gcacagttgc ttgctggtca agacgccaac ttggcaaggt   1440
tatgctgctg gcaaaggcag attcgtcaga ataaagtcgc cacaggctca accaggcaaa   1500
tcatgaatgg ccctttcagc aggagcctga gaggagggat gttattcagc ccagcaaccc   1560
tatttacttt ttttcaggat ccccaaactc gcgtttttta aggctttccg ctacaagaga   1620
gccaaaattg aagcctgggt tggcggcagt gcaggtacct gctcacctaa gcatccctct   1680
tttaattttc ctaactcctc caccc                                        1705
```

<210> SEQ ID NO 8
<211> LENGTH: 695
<212> TYPE: DNA
<213> ORGANISM: H. sapiens

<400> SEQUENCE: 8

```
aaagtatttc taggaaagta caaactattt aaaatcatta gttagttttg aactaaaatc     60
ctttaaaaat atacaacaaa aaaggtagtt tccagatgtc ctttacactg ttactgagaa    120
tgtaaaatgt cttcattaa tttggattct ttaaacattc ctctatgatc atatttaagt    180
gtgaaatttt actccctatt gttgtagata atcttttagt caggtaatga atagcacatg    240
gtacagaaaa acatatacat atacattttc atttcagctt ttctgaagcc ccattgttta    300
tttcaggctg ctttactgag actccttgca ctaaacgcct ctggttgcat tccactcaag    360
acaaaggcat attttaggga tgtacctctg acaagaggt atttatggac caggaatcag     420
actttggaca aatgggcatt tcattataac acagcctaat tgttaaagct cttattgaaa    480
agaataaaaa tttcattagt catcacagga actcagcaca aactcctcct ccttttcccc    540
acaatgcaca gaaagaatgg cagctttaag cttatcattg aacattttga aggctttggt    600
ccttccttcc ttttgttcca cttgcactaa gaagtatttt agtaacaatt gtgaaataac    660
tgtggtaata atttttaacga aattttataa atgta                               695
```

<210> SEQ ID NO 9
<211> LENGTH: 386
<212> TYPE: DNA
<213> ORGANISM: H. sapiens

<400> SEQUENCE: 9

```
tcttctgctc ctaagtgcag cacactgggg gaaaggaaag gccaaaagag ggagggtcat     60
caactgcaga gttccacggg gttccaggtg attgcaggtt ataaagcagc ttggtgcctg    120
tataggctta gtaaatcaag aagtgatgtt aagataatgg aaacagcctg ctttgtataa    180
atttgtttac tctgttctca ataggtaaca taatttgcat catatgctct atttatgaca    240
cacctggatt cagaaatgag gtcattaagt tataaacttc atctggttct tttgtgaaaa    300
atagacatca actattagcc cacttataaa ataacctgta taaattgtac cacctgtctc    360
catgaagcct cttcaagtgt tcacaa                                          386
```

<210> SEQ ID NO 10
<211> LENGTH: 1315
<212> TYPE: DNA
<213> ORGANISM: H. sapiens

<400> SEQUENCE: 10

```
cactgatttc ttgctttta catttcaaac tccaaaagtg tatttcaact attcatatga     60
tgattgaata aacttgtttt acattatgga acacccttac tgtgtagagc tgtgagaaat   120
```

-continued

```
tcaataatca gtatttaatg tggacaaaaa tagatagatt agagaaacaa taaacatgga      180
catatctaca cataatatat actccttttc tatccaaaaa tctgacaaaa accttacaca      240
atggtcagtt tacaccattt taaggacaag gatgtggtga aacaatttta aacattttta      300
tataataaaa gaaaaaagtt gttttaattg ctaatgatca agtttttacc aagaatttac      360
atatgcatca tcaaacagta gcttgaaact gaagcttgac ctttgagaaa taaagctttt      420
aaagtaaatg tctaaattct cttttcttta ttatgttaca tttcatttac tttaggtttt      480
ctagtgcaat ttaaataaga aataaataga gagtatggta atcaggtaca aaggctgtga      540
aaatattccc tgcattttgc acagggaata tgttcaaatt cctaatctgc aaagaagaaa      600
agtgcatttt ctttttttgaa atggcatttg aagatctctc catccatgaa cattcttgag      660
catatggatt ttacaataac agcagtgtat attagttttt taatttatca ttaactgata      720
acatatacag taaaatataa tttccgtttt cttatctaag ggcagaaaat cccaacctat      780
ttctgaatct cactttggaa caaggacaga atgacctgac atggcatttt tgatttccaa      840
cgtttaaacg cataacgttt gtgtgctatg gaagcatctt agcttctgga atttatgctc      900
gacacgaaac ataaacaata aacaattcag tccacgttat atagacatat ctcatatata      960
tatgagatat atatatataa aatatcttac gcacatgcac acttagactt tctcggtttt     1020
catgaaactc acaatctacc tcaggcgctc aaaggcactc ggcctctcag gtctgaggca     1080
ccacagagag gcttccttgg gcacagttgc ttgctggtca agacgccaac ttggcaaggt     1140
tatgctgctg gcaaaggcag attcgtcaga ataaagtcgc cacaggctca accaggcaaa     1200
tcatgaatgg ccctttcagc aggagcctga gaggagggat gttattcagc ccagcaaccc     1260
tatttacttt ttttcaggat ccccaaactc gcgttttta aggctttccg ctaca           1315
```